United States Patent [19]

Rose

[11] 4,089,332

[45] May 16, 1978

[54] PNEUMATIC SHAPING EAR PLUG

[76] Inventor: Leo J. Rose, 11560 Shadbust Ct., Reston, Va. 22091

[21] Appl. No.: 713,018

[22] Filed: Aug. 9, 1976

[51] Int. Cl.² ............................................. A61F 11/00
[52] U.S. Cl. ................................................... 128/152
[58] Field of Search ................................ 128/152, 151

[56] References Cited

U.S. PATENT DOCUMENTS 1,344,935   6/1920   Baum .................................. 128/152

FOREIGN PATENT DOCUMENTS 400,326   2/1974   U.S.S.R. .............................. 128/152

Primary Examiner—Robert W. Michell
Assistant Examiner—Henry J. Recla
Attorney, Agent, or Firm—George R. Douglas, Jr.; Sherman Levy

[57] ABSTRACT

A new and improved pneumatically shaped ear plug comprising and constructed of an elastomeric hollow body of sheet material dimensioned to and constructed for being inserted into the ear canal or ear cavity, and end of the cylindrical hollow body being of a material performing as a diaphragmatic member so that when it is depressed, the volume of air therein extends the cylindrical side, and vice versa, said end member having a lead or handle means for retracting said diaphragm when it is depressed for restoring it to its original condition, said end member being of such resiliency of said elastomeric material that it retains its depressed condition when it has been so depressed, and retains its released condition when it has been released, thereby constituting a dual state condition as operated upon by action on said diaphragmatic member.

1 Claim, 6 Drawing Figures

PNEUMATIC SHAPING EAR PLUG

CROSS-REFERENCE TO RELATED PRIOR INFORMATION AND ART

There are no known prior art information or data that teaches any of the present features of this invention insofar as is known to applicant and as applicant is informed from one having conducted a search of the Patent Office records, such as in Class 128.

BRIEF SUMMARY OF THE INVENTION

The invention relates to a new and improved pneumatically shaped conforming ear plug and more particularly, the invention is directed to and relates to such an improved pneumatically conforming ear plug for being contoured and shaped to be received within one's ear canal or ear cavity, that it is essentially retained therein when a diaphragmatic end member thereof exterior of said ear canal or cavity is depressed for extending the diameter of the cylindrical wall or side, and more particularly, the invention relates to such a device that provides for the diaphragmatic end member to retain its depressed condition state condition and when it is withdrawn therefrom by manual action, it retains its other or released state or condition.

More particularly, the invention relates to such a pneumatically shaped conforming ear plug device as described in which the device is retained, secured and held within the ear canal when the diaphragmatic member is depressed and it is easily withdrawn from said ear canal when the state or condition of the diaphragmatic member is withdrawn, such as by a pull or small force being applied to the depressed diaphragmatic member such as by a lead or handle means centrally disposed and connected to said diaphragmatic member.

The invention also relates to providing new and improved lead and handle means for adjusting one of the two resilient conditions or states of the diaphragmatic member and it is constructed so that it is terminated in a knob.

FIELD OF THE INVENTION

It is an object and advantage of the present invention to provide a new and improved ear plug apparatus which is adapted and constructed to be inserted as a ear plug and locking device for effecting and accomplishing essentially and substantially complete elimination of all noises from reaching one's ear drum, and to provide improved sound isolation device.

Another object and advantage of the invention is that it is a device which effects controlled elimination of unwanted background noise and sound and is advantageous for use in combination with other devices such as a stethoscope or hearing aid.

Another and further object and advantage of the present invention is to provide a new ear plug apparatus which completely eliminates all sound other than the sound which may be electronically received by a unit or sound transmittor element that may be implanted within the inner end of the new ear plug device.

It is a further object and advantage of the present invention to provide a new ear plug combination such that the ear plug feature of the combination may be inserted and essentially locked in place in the ear canal and to provide thereby substantially complete isolation of environmental noises from passing from the environment to one's ear organ.

A further and additional object of the present invention is to provide a construction which is adaptable to be inserted in one's ear while the other ear may be used in combination with a stethoscope, hearing aid mount, or device, or earphone, and thus one ear is useful for the reception of sound while the other one is used to provide the omission of any sound reaching it by means of the new and improved insertable ear plug locking device of the present invention.

BRIEF DESCRIPTION OF THE SEVERAL VIEWS OF THE DRAWING

The above and other objects and advantages of the invention will become apparent upon full consideration of the following detailed description and accompanying drawings in which.

DETAILED DESCRIPTION OF THE PREFERRED EMBODIMENT OF THE INVENTION

Figure 3:
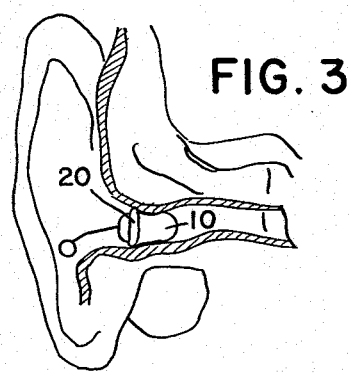
FIG. 3 is a cross-sectional and schematic view showing the plug ready to be inserted in one's ear canal according to the present invention.
Figure 4:
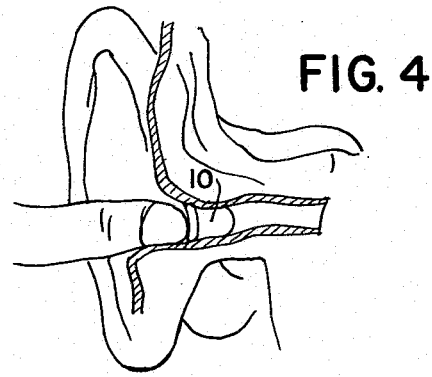
FIG. 4 is a cross-sectional and schematic view showing the manner in which the ear plug according to the present invention is locked in one's ear canal by the insertion of the finger upon the diaphragmatic element.
Figure 5:
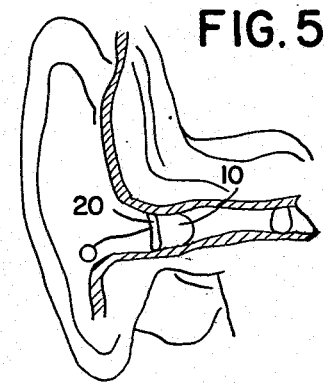
FIG. 5 schematically shows the ear plug locked in one's ear canal according to the practice of the present invention.

Referring now to the drawings there is shown a new ear plug 10 constructed of an elastomeric hollow body of sheet material 12 which is shown cylindrically contoured and shaped to be receivable within one's ear cavity or canal as shown in FIG. 3. An end 14 of the cylindrically hollow body is constructed of sufficient resiliency to perform as a diaphragmatic member so that when it is extended as shown in FIG. 1 it is in a state of structural and mechanical characteristic so that it remains in that state, but when it is depressed about its central area, when sufficient force is applied, the end 14 will be slipped into a second stable condition as shown in FIG. 3, and since the cylindrically hollow body is constructed with air-tight integrity, the peripheral walls of the cylindrically hollow body are radially distended so that it engages the ear canal as shown in FIGS. 4 and 5.

It is within the perview of the present invention to provide an annular ridge 20 about an outer circumference of the cylindrically hollow body of the ear plug 10 so that additional sound-tight integrity of the ear plug is provided to the user. The construction of the annular element 20 may be of the same construction of the material forming the cylindrically hollow body of the ear plug 10, or it may be of different material and formed separately, or in some cases, intergrally with the ear plug, as is shown in each of the Figures.

The annular element 20 possesses a configuration forming a ridged portion extending above an outer diameter or circumference of the ear plug 10 and also performs as a holding and guiding element for insertion of the ear plug within the ear canal.

Figure 1:
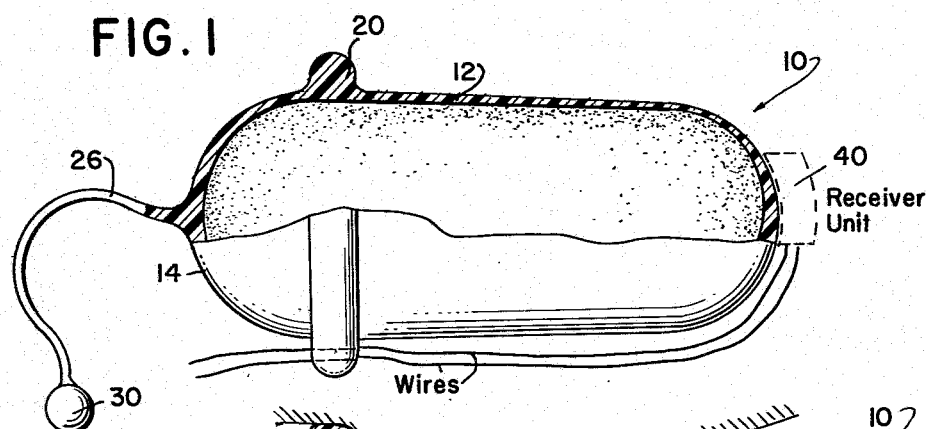
FIG. 1 is a side elevation view, partially broken away, and showing the preferred and best mode of the new and improved ear plug construction of the present invention.
Figure 6:
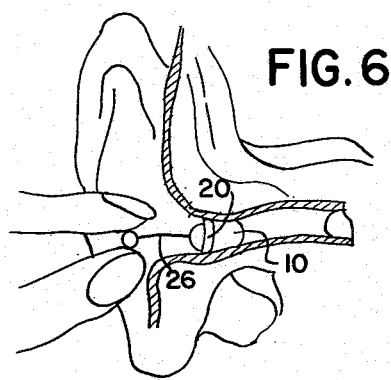
FIG. 6 shows the manner in which the ear plug is removed by pulling the release mechanism for the diaphragm and withdrawing the ear plug from one's ear canal.

There is intergrally secured to a central area of the diaphragmatic member 14 a lead member 26 which terminates at its free end in a handle or knob 30 so that when one exerts a force or pull upon the lead 26 or the knob 30, the diaphragmatic member 14 may be accordingly displaced from its inner stable position to its initial stable position as shown in FIGS. 1 and 6.

The ear plug of the present invention may be useful in many different environments, particularly for isolating sound from passing along one's ear canal, and when the ear plug of the present invention is properly secured and inserted within one's ear canal, the environmental sounds and noises are precluded from passing along and into the ear canal from reaching the ear membranne or ear drum of the person to which the ear plug is inserted and applied.

Within one embodiment of use of the present invention, there may be provided and installed a small sound producing unit 40 which may be part of a radio receiver or part of a typical earphone apparatus. The connecting wires may be disposed along one side of the ear plug as diagramatically shown in FIG. 1. The sound producing unit 40 may be of sufficient low power so that any sound produced thereby does not abuse the normal use of one's ear membrane, and because it is inserted within a closed and locked area of one's ear canal, it is found that the necessary power to actuate such sound producing unit 40 may be of unusually low sound power.

Figure 2:
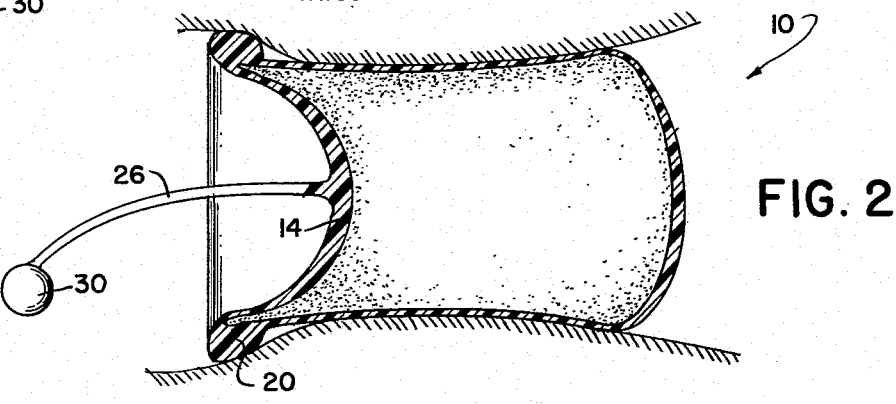
FIG. 2 is a cross-sectional view of the device according to claim 1 thus showing the diaphragmatic end surface being depressed.

Thus it is seen that by the practice of the present invention there is provided a new and improved insertable and locking ear plug that may be readily inserted into one's ear canal, and when the appropriate force is applied to the diaphragmatic, two state membrane 14 as shown and described in this specification, that upon applying the necessary force for changing the mechanical state of membrane 14 from that of FIG. 2 to that of FIG. 1, that the ear plug may accordingly be capable of being readily dislodged from the ear canal.

Additional embodiments of the invention in this specification will occur to others and therefore it is intended that the scope of the invention be limited only by the appended claims and not by the embodiment(s) described hereinabove. Accordingly, reference should be made to the following claims in determining the full scope of the invention. What is claimed is:

1. A new and improved pneumatically shaped-conforming ear plug and the like comprising an elastomeric hollow cylindrical body for being received within one's ear cavity, said cylindrical body having first and second closed ends and a finite volume of air therein and wherein the first closed end is comprised of a outwardly extending semi-spherically shaped diaphram which includes handle means mounted centrally thereon, said first and second closed ends having elastomeric consistency to perform as diaphragmatic members so that when said first closed end is depressed the second closed end is extended and vice versa, said handle means having a termination in a knob and being available to retract said first closed end when depressed to restore it to an original condition, said hollow cylindrical body possessing a ridge forming portion proximate to the first closed end and about an outer diameter of said cylindrical body for performing as a holding and guiding element for insertion within an ear, and said first closed end being essentially constructed and arranged in essentially hemispheric shape to operate as a two-state condition device.

* * * * *